United States Patent
Ma et al.

(10) Patent No.: US 9,976,906 B2
(45) Date of Patent: May 22, 2018

(54) LIGHT POLARIZATION STATE MODULATION AND DETECTION APPARATUSES AND DETECTION METHOD

(71) Applicant: Graduate School at Shenzhen, Tsinghua University, Shenzhen, Guangdong (CN)

(72) Inventors: Hui Ma, Guangdong (CN); Jintao Chang, Guangdong (CN); Honghui He, Guangdong (CN); Nan Zeng, Guangdong (CN); Yonghong He, Guangdong (CN); Ran Liao, Guangdong (CN); Shuqing Sun, Guangdong (CN); Zhenhua Chen, Guangdong (CN)

(73) Assignee: GRADUATE SCHOOL AT SHENZHEN, TSINGHUA UNIVERSITY, Shenzhen, Guangdong (CN)

( * ) Notice: Subject to any disclaimer, the term of this patent is extended or adjusted under 35 U.S.C. 154(b) by 34 days.

(21) Appl. No.: 15/202,717

(22) Filed: Jul. 6, 2016

(65) Prior Publication Data

US 2016/0313185 A1    Oct. 27, 2016

Related U.S. Application Data

(63) Continuation of application No. PCT/CN2015/070146, filed on Jan. 6, 2015.

(30) Foreign Application Priority Data

Jan. 6, 2014   (CN) .......................... 2014 1 0005298

(51) Int. Cl.
*G01J 4/00* (2006.01)
*G01J 4/04* (2006.01)

(52) U.S. Cl.
CPC ...................................... *G01J 4/04* (2013.01)

(58) Field of Classification Search
CPC ....................................................... G01J 4/00
(Continued)

(56) References Cited

U.S. PATENT DOCUMENTS 5,991,076 A   11/1999   Cheng
7,280,770 B2  10/2007   Tan et al.
(Continued)

FOREIGN PATENT DOCUMENTS

CN   1387071    12/2002
CN   101539458  9/2009
CN   103698015  4/2014

OTHER PUBLICATIONS

International Search Report issued in the corresponding International PCT Application No. PCT/CN2015/070146, dated Apr. 16, 2015, 6 pages.
Su et al., "Birefringent properties of diametrically loaded gradient-index lenses", Applied Optics, vol. 35, No. 24, Aug. 20, 1996, ISSN: 0003-6935, pp. 4772-4781, 10 pages.
(Continued)

*Primary Examiner* — Roy M Punnoose
(74) *Attorney, Agent, or Firm* — Hamre, Schumann, Mueller & Larson, P.C.

(57) ABSTRACT

Disclosed are a light polarization state detection apparatus, a detection method and a light polarization state modulation method. The light polarization state detection apparatus comprises a lens with a variable birefringence feature as an optical phase modulator, a polarizer as a SOP analyzer, a plurality of common lenses and a CCD as imaging devices, and a data processing and displaying unit. The SOP detection apparatus uses wide special birefringence distribution of birefringence optical elements such as a GRIN lens to obtain the Stokes parameters of light to be measured by CCD single frame imaging, and can rapidly accurately measure the SOP. The SOP detection apparatus is simple in structure, lower in
(Continued)

cost without containing any motion parts and electrical modulation devices, and is a fully static full Stokes parameters SOP detection apparatus.

9 Claims, 6 Drawing Sheets

(58) Field of Classification Search
USPC .......................................................... 356/364
See application file for complete search history.

(56) References Cited

U.S. PATENT DOCUMENTS

| | | | |
|---|---|---|---|
| 7,639,348 B2 * | 12/2009 | Niitsu | G01L 5/0047 356/33 |
| 9,442,015 B2 * | 9/2016 | Kudenov | G01J 3/2803 |
| 2003/0103214 A1 | 6/2003 | VanDelden | |
| 2005/0259907 A1 | 11/2005 | Tan et al. | |
| 2010/0045956 A1 * | 2/2010 | Van De Kerkhof | G01M 11/0264 355/71 |

OTHER PUBLICATIONS

Chang et al., "Single-shot spatially modulated Stokes polarimeter based on a GRIN lens", Optics Letters, Optical Society of America, vol. 39, No. 9, May 1, 2014, pp. 2656-2659, ISSN: 0146-9592, 4 pages.
The partial supplementary European Search Report of European Patent Application No. 15733176.0, dated Jul. 28, 2017, 12 pages.

* cited by examiner

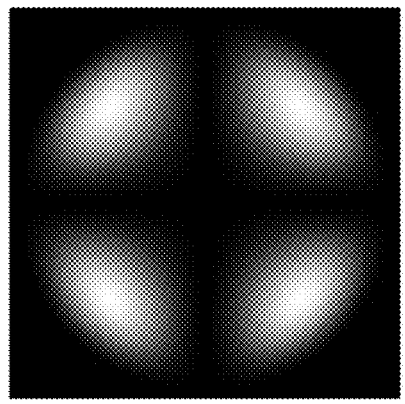
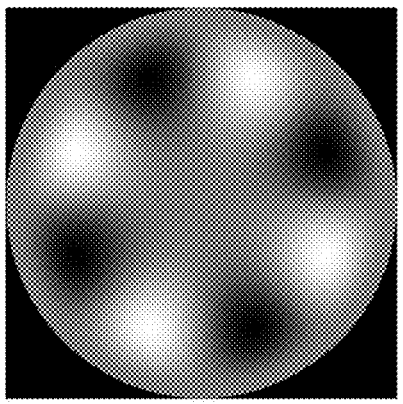
FIG. 9c          FIG. 9d
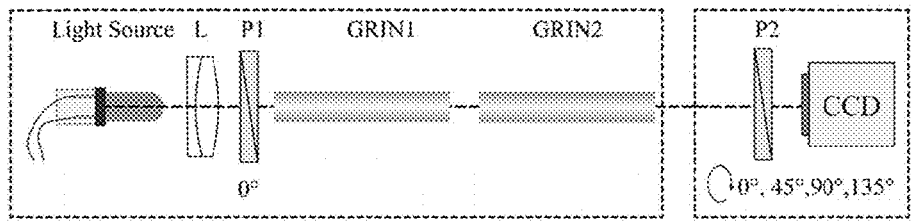
FIG. 10
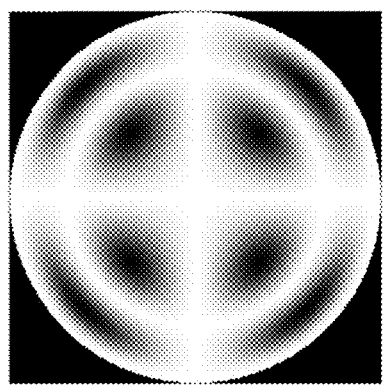
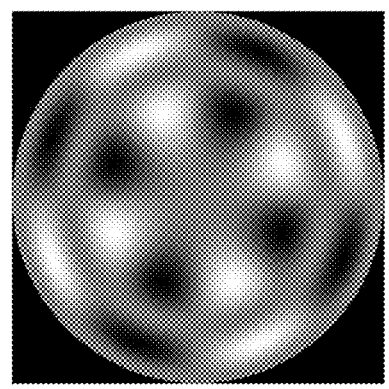
FIG. 11a         FIG. 11b

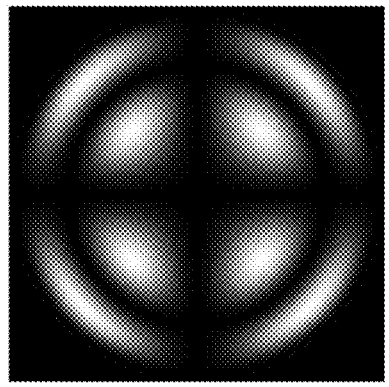
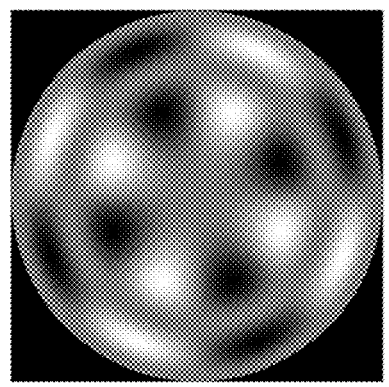
FIG. 11c　　　　FIG. 11d
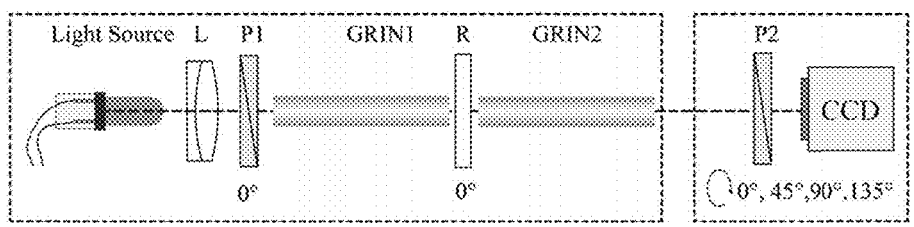
FIG. 12
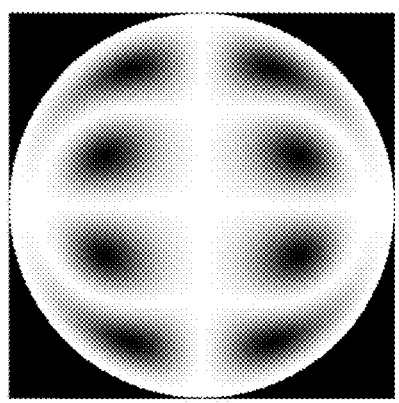
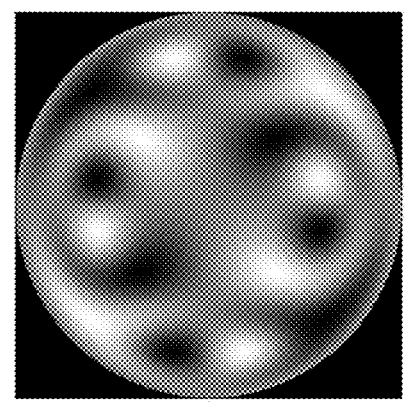
FIG. 13a　　　　FIG. 13b

LIGHT POLARIZATION STATE MODULATION AND DETECTION APPARATUSES AND DETECTION METHOD

BACKGROUND

Technical Field

The application relates to the state of polarization (SOP) of light modulation apparatus and a SOP detection apparatus, in particular to a modulation apparatus capable of modifying the SOP of light in three dimensional space to generate a polarization vector vortex field with spatial distribution and a SOP detection apparatus capable of measuring all Stokes parameters at high speed in real time, and a detection method thereof.

Related Art

Electromagnetic waves are transverse waves, and the state of polarization (SOP) of light is one of most important basic attributes of the light. In each optical field, the SOP of light is an important parameter. For example, in a remote sensing technology, a target object can be effectively recognized by detecting the light of specific SOP, in biomedicine photonics, polarization imaging can improve a resolution of the image and provide pathological change information, and in materials science, polarized light can be used for measuring parameters such as thickness and refraction index of a thin film.

The Stokes vector is required to determine all polarization information of a light beam and is a universal concept representing the SOP of the light, which can represent any SOP light, including linearly polarized light, circularly polarized light, elliptically polarized light and partially polarized light.

Measurement of the Stokes vector requires to measure the light intensity of the light passing a number of (more than or equal to 4) different polarization elements. In past dozens of years, various SOP detection apparatuses are invented in the world, aiming to realize accurate and fast measurement. In general, there are two types of SOP detection apparatuses: time-independent measuring apparatuses and simultaneous measuring apparatuses. The original SOP detection apparatus consists of a rotating crystal wave plate and a polarizer. Though it is simple in structure and mature in theory, the rotation of the wave plate or polarizer depends on manpower or a motor, at least four measurements are required, and the fast measurement requirements cannot be met. In addition, the rotation of the wave plate will cause light beam drifting, the whole system is non-static, as a result, the uncertainty of measurement is increased. The other type of SOP detection apparatus uses a liquid crystal wave plate (or electro-optical crystal) to replace a traditional crystal wave plate, it uses modulation voltage to rapidly change the phase retardance, although the measurement time is reduced, certain rapid measurement requirements are still not met. In addition, such SOP detection apparatus usually requires two or more liquid crystal (or electro-optical crystal) modulators, and the cost is higher.

Therefore, the simultaneous SOP detection apparatus is of great significance. The simultaneous measurement polarimeter (SMP) is usually realized by using wave-front division and amplitude division methods. A wave-front division apparatus generally requires a design of at least four independent miniaturized optical elements in the light path, and then corresponding signals of all elements are detected one by one. The amplitude division apparatus uses a beam splitter prism to divide a light path into more than four paths, each path with different path design, and the signal of each path is detected finally. The wave-front division apparatus has high requirements on micromachining process. The amplitude division apparatuses have more elements, usually larger in size and higher in cost. All kinds of apparatuses correspond to different measuring methods and their calibration work is very complex.

Known from above description, the SOP detection apparatuses have problems on synchronism, costs, stability and calibration difficulty more or less. A new SOP detection apparatus is urgently required.

On another aspect, a polarization vector vortex field with spatial distribution has many important uses, including multichannel light information transmission and polarization remote sensing measurement, singular optics research, multichannel polarization lighting and analysis, and single measurement of the optical axis direction of crystal, etc. At present, a two dimensional spatial phase modulation sheet prepared by some processes such as thin film processing exists in the market, but its price is high and has the defects that the modulation aperture is in-continuous and the modulation variety is not rich.

SUMMARY

A purpose of the present application is to provide light polarization state modulation and detection apparatuses with performance and price advantages and a light polarization state detection method to meet simultaneous measuring requirements.

For the purpose, the present application provides a light polarization state detection apparatus, comprising a polarizer, an imaging lens, a CCD, a data processing apparatus arranged in a light path in sequence, a data transmission line connected between the CCD, and a data processing apparatus; wherein the apparatus further comprises a lens with a variable birefringence feature, which can receive measured incident light and cause exit beams to generate the spatial phase modulation before entering the polarizer, light rays of different phases are subjected to polarization interference after passing the polarizer and generate an interference pattern, and interference fringes are projected on the CCD, recorded and transmitted to the data processing apparatus; the data processing apparatus calculates SOPs of different incident light according to the shapes of different interference patterns to which the SOP of different incident light corresponds; the lens with the variable birefringence feature is a device having certain birefringence parameters with certain special retardance distribution, including a birefringence value and an optical axis direction.

The present application further provides a light polarization state detection method, comprising the following steps: A, causing a light beam to be measured to enter a light inlet of a detection apparatus, wherein incident light has a certain SOP; B, causing the incident light to enter a lens with a variable birefringence feature to generate spatial phase modulation of a light field; C, causing the light emergent from the lens with the variable birefringence feature to enter a polarizer, wherein the light of different phases generates polarization interference after passing the polarizer and generate an interference pattern; D, causing the light to enter a CCD, wherein interference fringes are projected and recorded on the CCD; E, calculating SOPs of different incident light according to the shapes of different interference patterns to which the SOPs of different incident light corresponds.

The present application further provides a light polarization state modulation apparatus, comprising a polarizer and a lens with a variable birefringence feature arranged in a light path in sequence; the lens with the variable birefringence feature can modulate a SOP in a three dimensional space to generate a polarization vector vortex field with spatial distribution; the lens with the variable birefringence feature is a device having certain birefringence parameters with certain spatial retardance distribution, including a birefringence value and an optical axis direction.

The inventor provides the technical solution based on the fact that the inventor observes in an experiment that an original SOP of polarized light will be changed after the polarized light passes a GRIN lens or a material with variable birefringence, in the situation of the GRIN lens, such change is similar to the effect of plenty of annular micro wave plate arrays, the retardance of these micro wave plates is between 0~180 degrees, and a birefringence fast axis direction is distributed between −90~90 degrees, and can traverse all possible wave plates. The polarized light passes the wave plates of different retardance and optical axis directions, is subjected to a polarization interference phenomenon after passing the polarizer, and further forms distribution of different light intensity patterns on the CCD. These patterns correspond to the incident SOPs one to one. The present application can determine different incident SOPs by using different patterns, or extract parameters from different parameters to represent different SOPs.

The light polarization state detection apparatus based on the material with variable birefringence has the following advantages: firstly, simultaneous measuring requirements can be met; secondly, it requires no mechanical rotation, no electrically modulated phase optical elements, no excessive amplitude division or wave-front division elements, so that the cost is effectively reduced, the structure is compact and portable, and the apparatus can be easily applied to related systems and high in compatibility; thirdly, a static structure is adopted, performances are stable and use is simple; and fourthly, a very high system level precision can be realized and initial calibration of the system is rapid and accurate.

The light polarization state detection apparatus of the present application can be widely applied to various science research and industrial application occasions with SOP detection, and is specifically used for manufacturing various SOP detectors, ellipsometers, Mueller matrix measurement instruments, polarization remote sensing apparatuses, etc.

The light polarization state detection device of the present application has the characteristics of continuous modulation aperture and diverse types of modulation, and has obvious performance and price advantages compared with other polarization modulation devices prepared based on micro-nano machining on the market.

BRIEF DESCRIPTION OF THE DRAWINGS

FIGS. 9a-d are light intensity patterns of the polarization modulation corresponding to FIG. 8 at different polarization detection angles (0 degree, 45 degree, 90 degree and 135 degree).

FIG. 10 is a light path schematic diagram of polarization modulation of an embodiment 3 of the present application.

FIGS. 11a-d are light intensity patterns of the polarization modulation corresponding to FIG. 10 at different polarization detection angles (0 degree, 45 degree, 90 degree and 135 degree).

FIG. 12 is a light path schematic diagram of polarization modulation of an embodiment 3 of the present application.

FIGS. 13a-d are light intensity patterns 1 of the polarization modulation corresponding to FIG. 12 at different polarization detection angles (0 degree, 45 degree, 90 degree and 135 degree).

DETAILED DESCRIPTION

The present application uses the GRIN lens as a light polarization state detection modulation device to realize modulation and demodulation of a SOP, or the GRIN lens is taken as a polarization state generator (PSG) and polarization state analyzer (PSA).

Embodiment 1

The present embodiment is intended to explain a light polarization state detection apparatus and a detection method thereof using the GRIN lens.

The GRIN lens is also called as a gradient index lens, is a columnar optical lens of which the refractive index is gradually changed along the radial direction and has focusing and imaging functions.

When light in the air encounters other mediums, the transmission direction of light is changed due to different refractive indexes. The imaging of traditional lens is to use the generated optical length difference to condense light into one point by controlling the curvature of the surface of the lens.

Figure 1A:
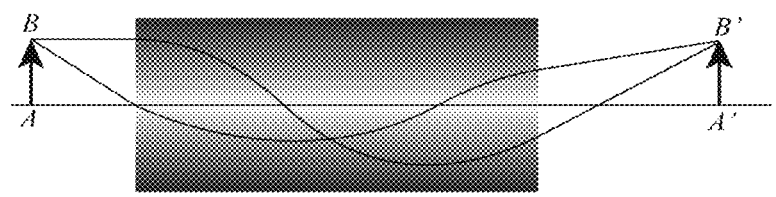
FIG. 1a is an imaging schematic diagram of a GRIN lens (the gray level represents the birefringence value, black is large and white is small).
Figure 1B:
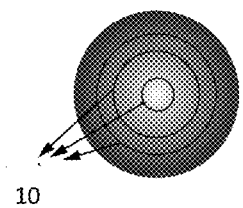
FIG. 1b is a cross section schematic diagram of a GRIN lens (the gray level represents the birefringence value, black is large and white is small).

The GRIN lens differs from a classical lens in that the GRIN lens material can cause light propagating along the axis direction to generate refraction, and the distribution of the refraction index is gradually reduced along the radial direction, to realize the emergent light convergence to a point smoothly and continuously. FIG. 1a shows a side section schematic diagram of a GRIN lens, wherein AB is an object, and A'B' is an image. Birefringence distribution of the GRIN lens used in the present embodiment is different from refractive index distribution, the birefringence value is gradually increased along a radial direction (the gray level is gradually increased from the center to the periphery), a fast axis direction 10 is along an annular direction of the GRIN lens (as shown in FIG. 1b), the gray level in the drawing represents the birefringence change and the birefringence is larger in the region with darker color.

Figure 2:
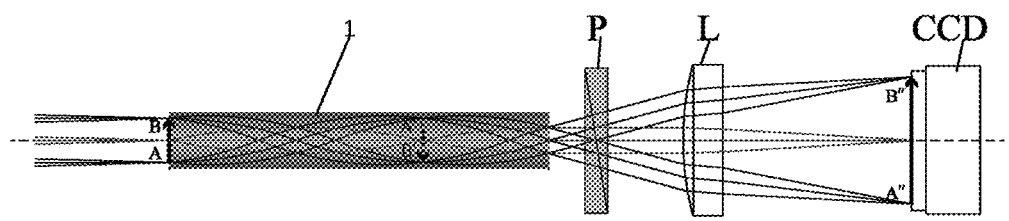
FIG. 2 is a schematic diagram of a SOP detection apparatus of an embodiment 1 of the present application.

The present embodiment is a simultaneous Stokes parameter detection instrument based on the GRIN lens, and as shown in FIG. 2, it comprises a housing, a GRIN lens 1, a polarizer P (with a fixed polarization angle), an imaging lens L, an area array charge-coupled device (CCD), a data transmission line, an electronic computer, and data processing, analysis, result displaying software. The GRIN lens 1, the polarizer P, the imaging lens L and the CCD are packaged in the housing. The length of the GRIN lens is centimeter magnitude, the whole SOP detection apparatus can be made to a length of 6 cm or even shorter, a diameter of 1.5 mm or even shorter, and is high in portability and compatibility. A memorizer or singlechip can be stored in the SOP detection apparatus and can independently work without the electronic computer. FIG. 2 is a light path diagram used by the present embodiment, the CCD is located in the imaging plane of the front surface of GRIN lens, wherein AB is an object and corresponds to the front surface of the GRIN lens, A'B' is an image in the GRIN lens and A"B" is an image in the CCD.

Figure 6:
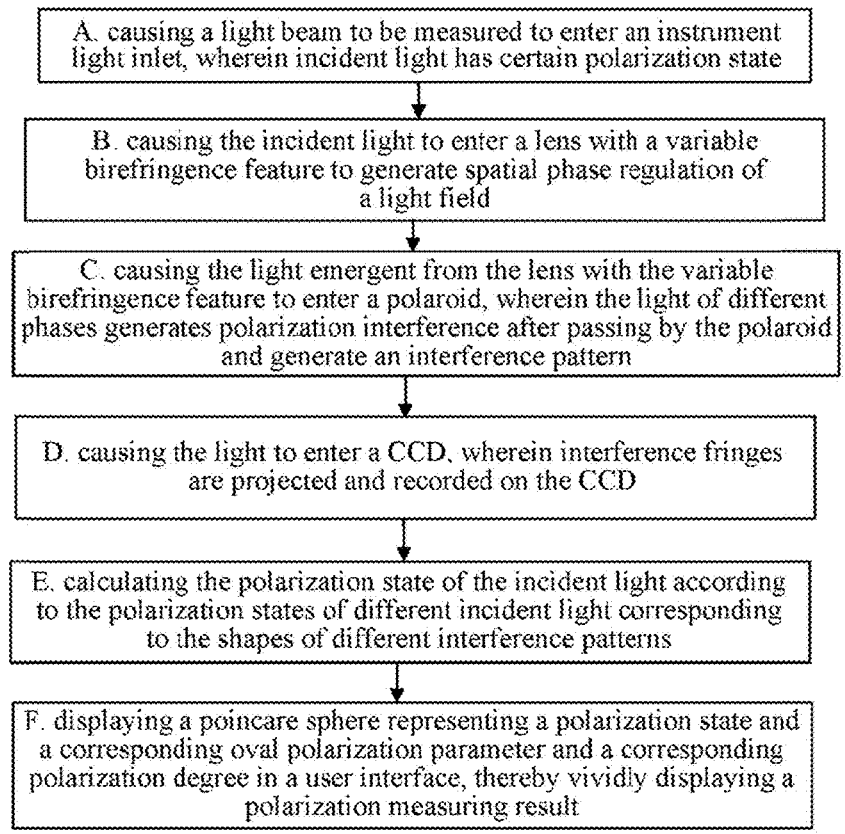
FIG. 6 is a flow schematic diagram of the embodiment 1 of the present application.

The present embodiment comprises the following measuring steps to perform polarization detection (as shown in FIG. 6):

A, causing a light beam to be measured to enter the light inlet of a detection apparatus, wherein incident light has a certain SOP, namely having intensity and phase distributions in x direction and y direction;

B, causing the incident light to enter a GRIN lens to generate spatial phase modulation of a light field;

C, causing the light emergent from the GRIN lens to enter a polarizer, wherein the light of different phases generates polarization interference after passing the polarizer and generate an interference pattern;

D, causing the light to enter a CCD, wherein interference fringes are projected and recorded on the CCD;

E, calculating the SOP of the incident light by certain specific pattern and storing, wherein different interference pattern shapes correspond to different SOPs of the incident light, that is, the SOPs of the incident light correspond to the patterns of the CCD one to one, and such one to one relation is built by a calculating program;

F, displaying a Poincare sphere representing SOPs and the corresponding elliptical polarization parameters in the user interface, thereby vividly displaying the polarization measuring result.

The principle of the method of the SOP detection apparatus is analyzed and explained as follows:

The incident light with different SOPs is projected on the CCD after passing the GRIN lens and the polarizer. In the process, the change of the SOP is $$S_{out} = M_P \cdot M_{GRIN} \cdot S_{in}$$

wherein, $S_{in}$ is the SOP of incident light, $S_{out}$ is the SOP of exit light at the CCD surface, $M_p$ is the Mueller matrix of the polarizer and $M_{GRIN}$ is the Mueller matrix of the GRIN lens.

The signal finally detected by the CCD is a light intensity signal and is only related to the first row of the Mueller matrix of the polarizer.

The first row of the Mueller matrix of the polarizer is $$M_P(1,:) = (p_x^2 + p_y^2, (p_x^2 - p_y^2)\cos 2\theta_P, (p_x^2 - p_y^2)\sin 2\theta_P, 0)$$

where $p_x$ and $p_y$ are extinction ratios of the exit light to the incident light in the minimal extinction direction and the maximal extinction direction of the polarizer, and $\theta_p$ is the azimuth angle of the minimal extinction direction of the polarizer.

When the incident beam is horizontally polarized, above formula can be simplified to be $$M_P(1,:) = (p_x^2\ p_x^2\ 0\ 0),$$

Figures 3A, 3B:
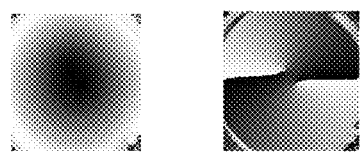
FIGS. 3a and 3b are schematic diagrams of retardance (the gray level represents the birefringence value, black is large and white is small (0~180 degrees)) and a birefringence fast axis direction (−90~90 degrees) of the GRIN lens of the embodiment 1 respectively.

It is found in the experiment that the retardance distributions and fast axis directions of the GRIN lens are as shown in FIG. 3a and FIG. 3b:

FIG. 3a is the phase retardance profile of the GRIN lens and FIG. 3b is the fast axis direction. The range of retardance is 0~180 degrees, the range of the fast axis angle is −90~90 degrees, which are results obtained by the measurement of Muller matrix.

Seen from the drawing, the birefringence distribution of the GRIN lens is annular symmetric. Polarization properties of different positions in the aperture of the GRIN lens are different, namely having different Mueller matrixes. For the purpose, the GRIN lens is divided into n micro regions, and if each micro region is small enough, the inside SOP can be considered to be the same. Each micro region is called as a sublens, correspondingly, the incident light is divided into n sub light beams, and each sub light beam corresponds to one sublens. The Mueller matrix of the nth sublens is $$M_{GRINn} \approx \begin{pmatrix} 1, & 0, & 0, & 0 \\ 0, & \cos^2 2\theta_n + \sin^2 2\theta_n \cos\delta_n, & 0.5\sin 4\theta_n(1-\cos\delta_n), & -\sin 2\theta_n \sin\delta_n \\ 0, & 0.5\sin 4\theta_n(1-\cos\delta_n), & \sin^2 2\theta_n + \cos^2 2\theta_n \cos\delta_n, & \cos 2\theta_n \sin\delta_n \\ 0, & \sin 2\theta_n \sin\delta_n, & -\cos 2\theta_n \sin\delta_n, & \cos\delta_n \end{pmatrix}$$

where $\delta_n$ and $\theta_n$ are the retardance and fast axis direction of the nth wave plate, respectively. $M_P$ in the formula is not required to be directly measured and can be directly used. The Mueller matrix $M_{GRIN}$ is obtained by the experiment in advance and the birefringence experiment result as shown in FIG. 3b can be derived from the $M_{GRIN}$. The $M_{GRIN}$ obtained by experiment is explained by $M_{GRINn}$ in an ideal form, in implementing, $M_{GRINn}$ can also be replaced by the element of the Mueller matrix of the GRIN lens for following calculating.

Assuming the incident light beam is n sub light beams, the GRIN lens consists of n tiny wave plates of different retardances and fast axis directions, correspondingly, n pixel light intensity values are obtained on the CCD, and the calculating formula of the light intensity of the nth pixel is $$s_{outn}^0 = p_x^2 s_{in}^0 + p_x^2(\cos^2 2\theta_n + \sin^2 2\theta_n \cdot \cos\delta_n) s_{in}^1 + 0.5 p_x^2 \sin 4\theta_n(1-\cos\delta_n) \cdot s_{in}^2 - p_x^2 \sin 2\theta_n \sin\delta_n \cdot s_{in}^3,$$

The formula can also be written in a matrix form $$I = A \cdot S_{in},$$

$$I = (s_{out1}^0\ s_{out2}^0\ s_{out3}^0\ \cdots\ s_{outn}^0)^T,,$$

-continued $$A = \begin{pmatrix} a_1^0 & a_1^1 & a_1^2 & a_1^3 \\ a_2^0 & a_2^1 & a_2^2 & a_2^3 \\ a_3^0 & a_3^1 & a_3^2 & a_3^3 \\ \vdots & \vdots & \vdots & \vdots \\ a_n^0 & a_n^1 & a_n^2 & a_n^3 \end{pmatrix},$$

$a_n^1 = p_x^2, a_n^1 = p_x^2 \cdot \cos^2(2\theta_n), a_n^2 = p_x^2 \cdot \cos^2(2\theta_n), a_n^3 = -p_x^2 \cdot \sin(2\theta_n)\sin(\delta),$ A pseudo-inverse calculating formula is adopted $$A_p^{-1} = (A^T A)^{-1} A^T,$$

wherein, $A^T$ is transposition of A, and $(A^T A)^{-1}$ is inverse of $(A^T A)$.

Finally, the incident SOP can be achieved via backstepping, $$S_{in} = A_p^{-1} \cdot I,$$

where I is the intensity value of each pixel on the CCD, A is a 4×n matrix, and $A_p^{-1}$ is a general inverse matrix of A, which are all known quantities during the calculation progress of $S_{in}$. $S_{in}$ has four unknown quantities, n light intensity values are obtained on the CCD, and n corresponds to the number of imaging pixels on the CCD, and is usually very large. It is equivalent to solve a linear equation system, there are four unknown numbers and n equations. In order to solve this overdetermined equation set, a solving process can refer to a pseudo-inverse algorithm, which can automatically obtained optimal solution by the least-square estimate method. Through theoretical calculation, generally, the accuracy of measurement will increase with the increase of n.

Equally weighted variance (EWV) represents a measuring error tolerance of the system. The smaller the EWV, the higher the tolerance.

$$EWV = \sum_{j=1}^{3} \sum_{k=0}^{N-1} (A_p^{-1})_{j,k}^2 = Tr[(A_p^{-1})^T A_p^{-1}] = \sum_{j=0}^{R-1} 1/\mu_j^2$$

where $W^+$ is pseudo-inverse of W, and Tr means the matrix trace.

Of course, not all the n light intensities and n equations are all necessary.

Condition number (k(A)) of matrix is adopted to seek for an optimal instrument matrix, the minimal condition number of a matrix is 1, and the solving of the linear equation system is more precise if the condition number is closer to 1. Two types of condition number are defined as follows $$k(A) = \|A\| \|A^{-1}\|,$$

$$\|A\|_2 = \sup_x \frac{\|A \square x\|_2}{\|x\|_2}$$

By balancing the optimal EWV and condition number, an annular region of certain retardance is selected to ensure measuring precision. Through formula $$S_{in} = A_p^{-1} \cdot I,$$

we can obtain the SOP of the incident light $S_{in}$.

$$S_{in} = A_p^{-1} \cdot I,$$

$$\begin{pmatrix} s_{in}^0 \\ s_{in}^1 \\ s_{in}^2 \\ s_{in}^3 \end{pmatrix} = A_p^{-1} \cdot (s_{out1}^0 \ s_{out2}^0 \ s_{out3}^0 \ \cdots \ s_{outn}^0),$$

Wherein $$A = \begin{pmatrix} a_1^0 & a_1^1 & a_1^2 & a_1^3 \\ a_2^0 & a_2^1 & a_2^2 & a_2^3 \\ a_3^0 & a_3^1 & a_3^2 & a_3^3 \\ \vdots & \vdots & \vdots & \vdots \\ a_n^0 & a_n^1 & a_n^2 & a_n^3 \end{pmatrix},$$

Figure 4:
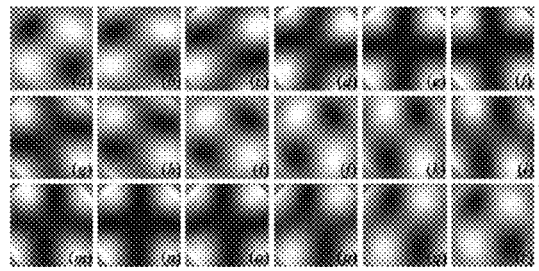
FIG. 4 is a schematic diagram of light intensity distribution patterns measured on a CCD of the embodiment 1 of the present application.
Figure 5:
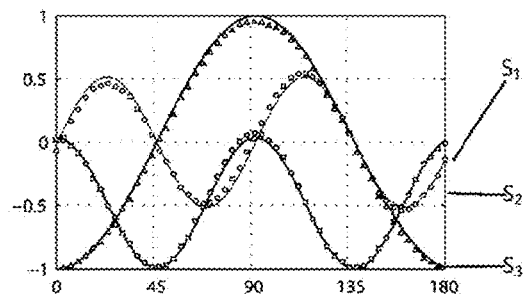
FIG. 5 is a schematic diagram of experimental and calculated Stokes parameters corresponding to different incident SOPs of the embodiment 1 of the present application in certain case.

Experimental verification of the present embodiment:

Monochrome parallel light is obtained by a method of introducing collimated LED light into a narrow-band filter (central wave length is 633 nm and full width at half maximum is 3 nm), and then the light is introduced into a polarized polarizer and ¼ wave plate. In the present embodiment, the polarizer is fixed at a certain angle, the ¼ wave plate is rotated, the light intensity measured on the CCD is shown in FIG. 4 (FIG. 4 shows a corresponding light intensity pattern on the CCD when the wave plate is rotated by 180 degrees and the polarizer in the PSG is fixed). FIG. 4 shows a-r eighteen schematic patterns in the 180 degree rotating process of the wave plate, each pattern selects n pixels, and the light intensity of the nth pixel is $s_{outn0}$. FIG. 5 shows SOPs $s_{in1}$, $s_{in2}$, $s_{in3}$ of the incident light obtained by calculating the light intensity patterns on the CCD and are normalized by $s_{in0}$. FIG. 5 shows Stokes parameters of the incident derived form 54 light intensity patterns of the CCD when the polarizer in the PSG is fixed and the wave plate is rotated by 180 degrees, theoretical ideal curves are $S_1$, $S_2$, $S_3$, experimental result is that square marker is close to $S_1$, circle marker is close to $S_2$ and triangle marker is close to $S_3$, in FIG. 5, the transverse axis is angle θ (degree) and the longitudinal axis is the normalized value of the Stokes parameters.

Measuring patterns and results of completely polarized light are listed above. Partially polarized light or natural light can also be measured in a single-shot.

Seen from above, the present embodiment can realize the accurate measuring of the SOP and has a lot of advantages:

1, the SOP of incident light can be determined by single frame picture, and simultaneous measuring requirements can be met;

2, the apparatus is a full static system without the need of any mechanical rotation devices;

3, the apparatus does not need any electrical phase modulation optical element (which are easily affected by outside factors such as temperature and has high requirement on modulation power source), so that the system is less influenced by electric signal, low in error and much more stable;

4, no excessive amplitude division or wavefront division elements are required, so that the cost is effectively reduced, the structure is compact and portable, and the apparatus can be easily applied to related systems and high in compatibility;

5, compared with most SOP detection apparatuses at present, initial calibration of the system is rapid and accurate, parameter selection can be optimized by a built-in algorithm through one-click, thereby greatly improving easiness in use and reducing the labor of an operator in instrument debugging;

6, the system has simultaneous measurement, low cost, stability, universality and easiness in use and is simple in structure, stable in performance, and low in cost and can be applied to various complex occasions.

There are many flexible implementing methods to demodulate SOP with the GRIN lens, for example:

1, above discussion aims at certain wave length, the experimental result is obtained by an LED red light source with a center wave length of 633 nm and a band width of 3 nm. In fact, analysis of other specific wave lengths is similar. The SOP detection apparatus has wide wave length measuring range as long as the incident light is a narrow band beam.

2, above method is only limited to the incident light with a uniform SOP, thus this is point measurement, which has one requirement that the SOP of the incident light in the aperture of the GRIN lens is uniform. The GRIN lens can also realize measurement of area imaging. The diameter of the GRIN lens can be as small as 0.1 mm and massive GRIN lenses can constitute m×n lens system, each GRIN lens corresponds to one point measurement and the spatial SOP distribution of the m×n size is finally obtained.

3, the present embodiment is explained by the GRIN lens, its phase distribution is shown in FIG. 3a and covers the retardance of 0~180 degrees and the fast axis angles of −90~90 degrees, and such distribution traverses all possible planar birefringence and has the largest error tolerance. But the method is not limited to the GRIN lens and is universal to process the SOP detection apparatus with any retardance devices as long as the Mueller matrix of the retardance devices is known. For example, if a thin film is designed with a larger retardance and fast axis angle range, it can also constitute the polarization measuring instrument by directly using the method in the specification. Therefore, the present SOP detection method is suitable for not only the GRIN lens but also other variable birefringence material.

4, the SOP detection apparatus can be used in various ellipsometers, Mueller matrix measurement instruments, polarization remote sensing apparatuses, etc. The application of the self-focusing devices to above three aspects or similar fields also belongs to the scope of the present invention.

The embodiment 1 and the flexible implements use the GRIN lens to demodulate SOP. The inventor also finds that the GRIN lens can be used to modulate SOP, that is, the GRIN lens is used to modulate SOP of light in a three dimensional space to generate a polarization vector vortex field with spatial distribution, which is explained by following embodiments 2-5.

The GRIN lens is used to modulate SOP to generate the polarization vector vortex field with spatial distribution. The vortex field comprises all of the possible SOP, namely GRIN lens generates all SOPs on the Poincare sphere. Meanwhile, the GRIN lenses with different intercepts in the production process are used to generate different phase modulations. As above mentioned, at present some two dimensional phase modulation plates prepared by a process such as thin film processing exist in the market and have high price, while the GRIN lens as a phase modulator can replace the existing phase modulation plates, has a low price, and can generate three-dimensional phase modulation.

Considering an example, when a horizontal linear polarization light enters the GRIN lens, the Stokes vector of exit light is $$S_{Out} = \begin{pmatrix} 1 \\ \cos^2 2\theta_n + \sin^2 2\theta_n \cos\delta_n \\ \sin 2\theta_n \cos 2\theta_n (1 - \cos\delta_n) \\ \sin 2\theta_n \sin\delta_n \end{pmatrix}$$

where $\theta_n$ and $\delta_n$ range from 0~180 degrees. Thus $S_{out}$ can traverse all SOPs.

The polarization angle can be written as $$AoP = \frac{1}{2} \cdot \arctan \frac{\sin 2\theta_n \cos 2\theta_n (1 - \cos\delta_n)}{\cos^2 2\theta_n + \sin^2 2\theta_n \cos\delta_n}$$

It can be seen that AoP relates to values of $\theta_n$ and $\delta_n$, in other words, AoP values are different in different positions.

The proportion of circularly polarized light is $$\frac{S_{Out3}}{S_{Out0}} = \sin 2\theta_n \sin\delta_n$$

In the formula, the plus sign represent right-handed elliptically polarized light, the negative sign represent left-handed elliptically polarized light. The proportion values are related to $\theta_n$ and $\delta_n$, which means that the proportions of circularly polarized light are different in different proportion.

Figure 7:
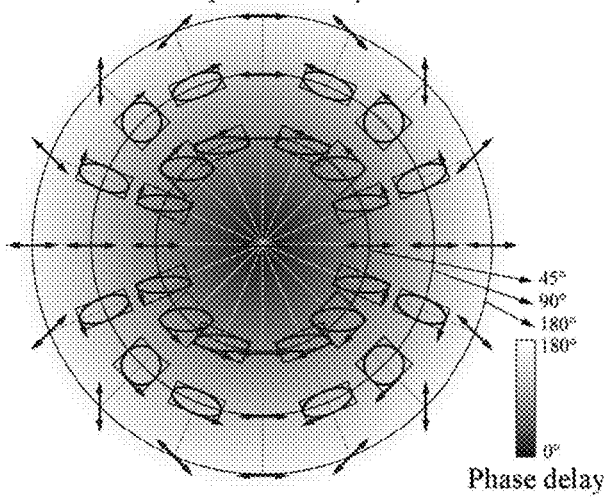
FIG. 7 is a schematic diagram of the exit SOP across the section modulated by the GRIN lens when the incident beam is horizontal linear polarized.

FIG. 7 shows the distribution of the exit SOP ($S_{out}$) across the section when the incident beam ($S_{in}$) is horizontal linear polarized, namely a schematic diagram of the polarization light modulated by the GRIN lens at certain section. It contains all possible linear polarized light, right-handed, left-handed circularly polarized light and elliptically polarized light.

The uses of polarization vector vortex field with the spatial distribution include the following several aspects:

(1) polarization remote sensing measuring and multichannel light information transmission in free space. As shown in FIG. 7, the GRIN lens can convert the horizontally polarized light into any possible polarized light, for example, generate the linearly polarized light in any direction in the peripheral region of the 180 degree retardance. Such one-to-many manner can improve the band width of light communication;

(2) the polarization vector vortex field generated by the GRIN lens contains many optical singular points and can be used for singular optics research and optical orbital angular momentum research;

(3) for the simultaneous spatial polarization state generator, multichannel polarization lighting and analysis, that is, the GRIN lens is used to irradiate a sample to be detected, polarization light received in different positions of the sample are different, and high pass measuring can be performed;

(4) for the simultaneous spatial polarization state generator, measuring the optical axis direction of crystal in a single shot, that is, the GRIN lens is used to irradiate the crystal to be detected, the polarized light received by different positions of the crystal are different, and detection results of different positions are considered comprehensively to determine the optical axis direction of the crystal;

(5) for the simultaneous spatial polarization state generator, and the Mueller matrix measuring of a sample can be realized in a single shot by combining the simultaneous polarization detection apparatus namely a GRIN lens polarization analyzer.

Embodiment 2

Figure 8:
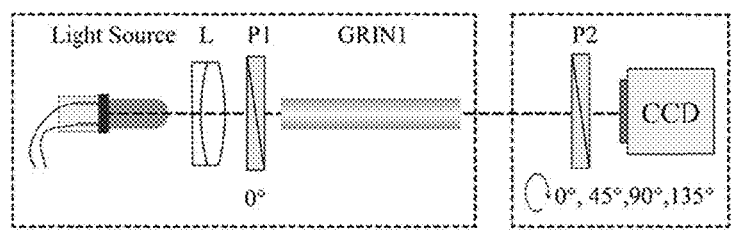
FIG. 8 is a light path schematic diagram of polarization modulation of an embodiment 2 of the present application.
Figures 9A, 9B:
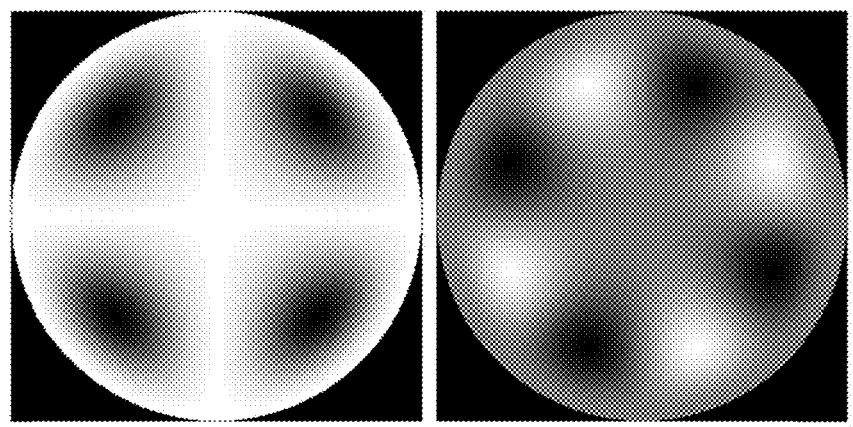
Figure 13C:
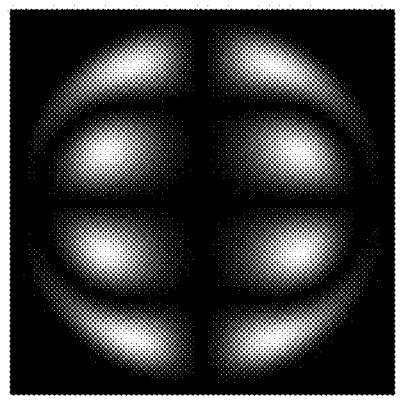
Figure 13D:
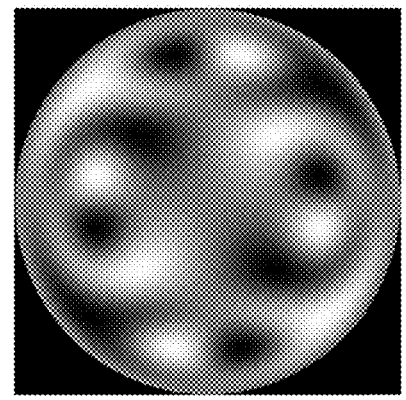
Figure 14A:
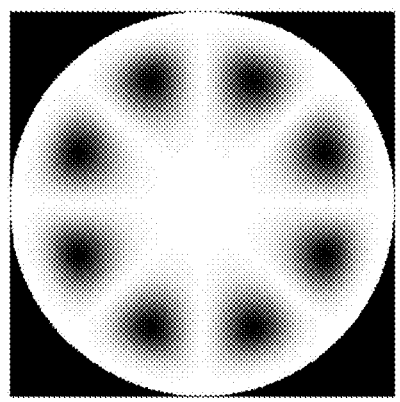
FIGS. 14a-d are light intensity patterns 2 of the polarization modulation corresponding to FIG. 12 at different polarization detection angles (0 degree, 45 degree, 90 degree and 135 degree), wherein used wave plates different from those in FIG. 13.
Figure 14B:
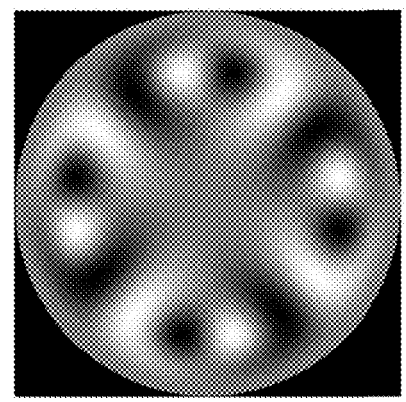
Figure 14C:
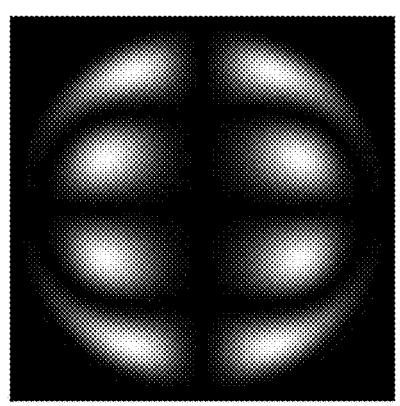
Figure 14D:
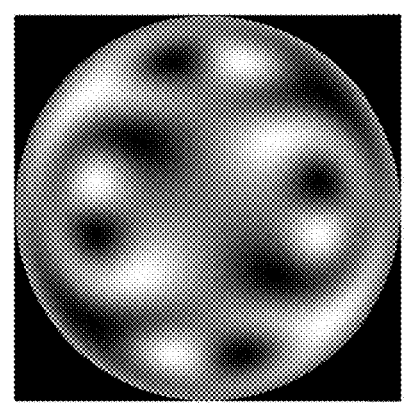

A light path is as shown in FIG. 8, light from a light source is collimated by a lens group L and enters a GRIN lens GRIN 1 after passing a polarizer in a horizontal 0 degree direction (or other directions, the horizontal direction is taken as an example herein), thus finishing the SOP modulation. The back module is a polarization analyzer consisting of a polarizer P2 with four polarization angles of 0, 45, 90 and 135 degrees, and the CCD is an imaging detector, wherein the polarizer is a SOP analyzer, and the wave plates with different retardance are used for assisting the optical phase modulation.

By using the polarization modulation solution in FIG. 8, some specific distributions of polarization state can be generated. In order to visualize polarization distribution, the P2 is rotated by four angles to record light intensity patterns on the CCD, and FIGS. 9a, 9b, 9c and 9d correspond to the situations that the P2 is at the four polarization angles of 0, 45, 90 and 135 degrees, respectively.

Embodiment 3

A light path is shown in FIG. 10, light from a light source is collimated by a lens group L and enters a GRIN lens GRIN 1 and a GRIN lens GRIN 2 after passing a polarizer in a horizontal 0 degree direction (or other directions, the horizontal direction is taken as an example herein), thus finishing the SOP modulation. The back module is a polarization analyzer consisting of a polarizer P2 with four polarization angles of 0, 45, 90 and 135 degrees, and the CCD is an imaging detector.

By using the polarization modulation solution in FIG. 10, some specific distributions of polarization state can be generated. In order to visualize polarization distribution, the P2 is rotated by four angles to record light intensity patterns on the CCD, and FIGS. 11a, 11b, 11c and 11d correspond to the situations that the P2 is at the four polarization angles of 0, 45, 90 and 135 degrees, respectively.

Embodiment 4

A light path is as shown in FIG. 12, light from a light source is collimated by a lens group L and enters a GRIN lens GRIN 1 after passing a polarizer in a horizontal 0 degree direction (or other directions, the horizontal direction is taken as an example herein) and then enters a GRIN lens GRIN 2 after passing R (a ¼ wave plate in the embodiment), thus finishing the SOP spatial modulation. The back module is a polarization analyzer consisting of a polarizer P2 with four polarization angles of 0, 45, 90 and 135 degrees, and the CCD is an imaging detector.

By using the polarization modulation solution in FIG. 12, some specific distributions of polarization state can be generated. In order to visualize polarization distribution, the P2 is rotated by four angles to record light intensity patterns on the CCD, and FIGS. 13a, 13b, 13c and 13d correspond to the situations that the P2 is at the four polarization angles of 0, 45, 90 and 135 degrees, respectively.

Embodiment 5

A light path is still as shown in FIG. 12, light from a light source is collimated by a lens group L and enters a GRIN lens GRIN 1 after passing a polarizer in a horizontal 0 degree direction (or other directions, the horizontal direction is taken as an example herein) and then enters a GRIN lens GRIN 2 after passing R (a ½ wave plate different from that in the embodiment 4), thus finishing the SOP spatial modulation. The back module is a polarization analyzer consisting of a polarizer P2 with four polarization angles of 0, 45, 90 and 135 degrees, and the CCD is an imaging detector.

By using the polarization modulation solution in FIG. 12, some specific distributions of polarization state can be generated. In order to visualize polarization distribution, the P2 is rotated by four angles to record light intensity patterns on the CCD, and FIGS. 14a, 14b, 14c and 14d correspond to the situations that the P2 is at the four polarization angles of 0, 45, 90 and 135 degrees, respectively.

The embodiments 2-5 explain four different embodiments using the GRIN lens to perform spatial polarization modulation, and the use of more GRIN lenses or the GRIN lenses with different lengths and different wave plates can generate more different spatial polarization modulations. Here cannot be exhausted.

The GRIN lens as the spatial polarization modulation device has the characteristics of continuous modulation aperture and diverse types of modulation, and has significant performance and price advantages compared with other polarization modulation devices prepared based on micro-nano machining on the market.

What is claimed is:

1. A light polarization state detection apparatus, comprising a polarizer, an imaging lens, a CCD and a data processing apparatus arranged in a light path in sequence and a data transmission line connected between the CCD and the data processing apparatus; wherein the apparatus further comprises a lens with a variable birefringence feature, which can receive measured incident light and cause emergent light rays to generate spatial phase modulation of SOP of a light field and then enter the polarizer, light rays of different phases are subjected to polarization interference after passing the polarizer and generate an interference pattern, and interference fringes are projected on the CCD, recorded and transmitted to the data processing apparatus; the data processing apparatus calculates SOPs of different incident light according to the shapes of different interference patterns to which the SOPs of different incident light corresponds; the lens with the variable birefringence feature is a device having certain birefringence parameters with certain spatial retardance distribution, including a birefringence value and an optical axis direction.

2. The light polarization state detection apparatus according to claim 1, wherein the data processing apparatus is an external computer or a combination of a memorizer, a singlechip and a display screen packaged in the SOP detection apparatus.

3. The light polarization state detection apparatus according to claim 1, wherein the lens with the variable birefringence feature is a GRIN lens.

4. The light polarization state detection apparatus according to claim 3, wherein one GRIN lens is arranged to realize SOP single point detection, or more GRIN lenses are arranged to form a m×n lens array and realize measurement in a SOP plane, each GRIN lens corresponds to one point for measurement to finally obtain spatial SOP distribution of m×n size, wherein m and n are positive integers.

5. The light polarization state detection apparatus according to claim 3, wherein the retardance distribution of the GRIN lens covers retardance of 0~180 degrees and a fast axis angle of −90~90 degrees.

6. The light polarization state detection apparatus according to claim 3, wherein the SOP detection apparatus is capable of being applied to an ellipsometer, a Mueller matrix measurement instrument and a polarization remote sensing apparatus.

7. A light polarization state detection method, comprising the following steps:
- A, causing a light beam to be measured to enter a light inlet of a detection apparatus, wherein incident light has a certain SOP;
- B, causing the incident light to enter a lens with a variable birefringence feature to generate spatial phase modulation of SOP of a light field;
- C, causing the light emergent from the lens with the variable birefringence feature to enter a polarizer, wherein the light of different phases generates polarization interference after passing the polarizer and generate an interference pattern;
- D, causing the light to enter a CCD, wherein interference fringes are projected and recorded on the CCD;
- E, calculating SOPs of different incident light according to the shapes of different interference patterns to which the SOPs of different incident light corresponds.

8. The light polarization state detection method according to claim 7, wherein the method further comprising a step F:
displaying a Poincare sphere representing the SOP and the corresponding elliptical polarization parameters and a corresponding polarization degree in the user interface, thereby vividly displaying a polarization measuring result.

9. The light polarization state detection method according to claim 7, wherein the lens with the variable birefringence feature is a GRIN lens.

* * * * *